United States Patent [19]

Lauks et al.

[11] Patent Number: 5,779,650
[45] Date of Patent: Jul. 14, 1998

[54] FLUID SAMPLE COLLECTION AND INTRODUCTION DEVICE AND METHOD

[75] Inventors: Imants R. Lauks, Rockcliff Park, Canada; Joseph W. Rogers, Doylestown, Pa.

[73] Assignee: i-STAT Corporation, Princeton, N.J.

[21] Appl. No.: 470,871

[22] Filed: Jun. 6, 1995

Related U.S. Application Data

[62] Division of Ser. No. 144,966, Oct. 28, 1993, abandoned.

[51] Int. Cl.$^6$ ............................................. A61B 5/00
[52] U.S. Cl. .................................................. 600/576
[58] Field of Search ............................. 128/760, 763, 128/765, 766, 770, 771; 604/51, 52, 132, 181, 183, 185; 422/61, 68.1

[56] References Cited

U.S. PATENT DOCUMENTS

| | | | |
|---|---|---|---|
| 852,065 | 4/1907 | Keller | 604/183 |
| 2,511,469 | 6/1950 | Hawks | 604/185 |
| 3,640,267 | 2/1972 | Hurtig et al. | 128/2 |
| 3,993,070 | 11/1976 | Sneider | 604/132 |
| 4,228,808 | 10/1980 | Marsoner | 128/762 |
| 4,263,922 | 4/1981 | White | 128/763 |
| 4,272,245 | 6/1981 | Diamond et al. | 23/230 B |
| 4,298,011 | 11/1981 | Mangurten et al. | 128/763 |
| 4,314,570 | 2/1982 | Sarstedt | 128/763 |
| 4,393,882 | 7/1983 | White | 128/764 |
| 4,436,098 | 3/1984 | Kaufman | 128/766 |
| 4,576,185 | 3/1986 | Proud et al. | 128/760 |
| 5,048,539 | 9/1991 | Schindele | 128/771 |
| 5,080,865 | 1/1992 | Leiner et al. | 422/68.1 |
| 5,096,669 | 3/1992 | Lauks et al. | 422/61 |
| 5,228,350 | 7/1993 | Karpf et al. | 73/864.81 |
| 5,257,984 | 11/1993 | Kelley | 604/403 |
| 5,309,924 | 5/1994 | Peabody | 128/765 |
| 5,351,563 | 10/1994 | Karpf et al. | 73/864.84 |

*Primary Examiner*—Max Hindenburg
*Attorney, Agent, or Firm*—Pennie & Edmonds LLP

[57] ABSTRACT

A device and method for collecting a fluid sample and introducing it into a sensing device for real time analysis providing flexibility and simplicity in the way sample fluid sample collection is accomplished and cooperating with a disposable cartridge of the sensing device to permit quick and easy sample introduction and eliminate the risk of sample spillage. an exemplary embodiment of the collection device includes a capillary tube capable of receiving or drawing a fluid sample and introducing the fluid sample into the disposable cartridge, a reservoir chamber capable of receiving a fluid sample and a capillary tube holder capable of supporting one end of the capillary tube in the reservoir chamber to draw the fluid sample by is capillary action. Alternative embodiments of the invention are used in combination with the variety of blood collection assemblies employed by the medical industry to collect fluid samples.

15 Claims, 11 Drawing Sheets

FLUID SAMPLE COLLECTION AND INTRODUCTION DEVICE AND METHOD

This is a division, of application Ser. No. 08/144,966, filed Oct. 28, 1993, now abandoned.

BACKGROUND OF THE INVENTION

The present invention relates to a device and method for collecting a volume of blood or other fluids in a capillary tube for diagnostic testing. More specifically, the invention relates to a device a and method for collecting a fluid sample and introducing it into a sensing device for real time analysis.

The present invention is contemplated to be used in conjunction with the disposable sensing device taught by U.S. Pat. No. 5,096,669 to Lauks, et al., the disclosure of which is herein incorporated by reference. The patent teaches a system comprising a disposable cartridge and hand-held reader for performing a variety of measurements on blood and other fluids. The disposable cartridge is constructed to serve a multiplicity of functions including sample collection and retention, sensor calibration and measurement.

A fluid sample, typically blood, is introduced into the disposable cartridge through an orifice at one end of the cartridge. The sample enters the cartridge by putting the orifice in contact with the sample. The sample is drawn by capillary action into a conduit in the cartridge, the conduit having the orifice at-one end and a capillary break at the other end. After the sample fills the conduit, the orifice is sealed off. The capillary break serves to contain the sample in the conduit until the sensors of the sensing device are ready, i.e. sensor calibration is performed. When the sensors are calibrated, the sample is forced across the capillary break past the sensors by operation of an air bladder. When the air bladder is depressed, air is forced into the orifice end of the conduit which forces the sample out of the other end of the conduit past the capillary break and across the sensors, where measurements are performed.

To test, for example, a patient's blood, a phlebotomist (as used herein, the term "phlebotomist" shall include without limitation physicians, technicians, nurses and other similar personnel) may prick the patient's finger with a finger stick to draw a small amount of blood through a dermal puncture. The phlebotomist places the orifice of the cartridge on the blood formed on the dermal puncture in the patient's finger. The blood is automatically drawn into the conduit by capillary action. Blood fills the conduit up to the capillary break. Alternatively, known capillary or syringe structures may be used to collect a sample from the dermal puncture. The capillary or syringe is then transported to and put in contact with the orifice of the cartridge and the sample is deposited therein.

The sensing device disclosed in Lauks has provided the phlebotomist with the much needed capacity to obtain immediate, reliable and accurate testing of fluid samples without the processing delays associated with traditional laboratories. Moreover, the sensing device has greatly reduced the quantity of fluid sample required to be drawn from the patient's body to run these tests.

Nevertheless, experience with use of the cartridge in the hospital environment has demonstrated limitations associated with introducing fluid sample into the cartridge of the sensing device by putting the orifice in contact with the sample. Because the cartridges are not reusable, once the sample has been introduced into the cartridge through the orifice, the cartridge must be analyzed or discarded. If the sample does not fill the cartridge properly, the entire cartridge is wasted and must be discarded and a replacement cartridge must be supplied.

Another limitation associated with the prior art introduction method relates to the accuracy with which the transfer of fluid sample from the dermal puncture or the capillary tube or syringe to the orifice is made. To minimize the quantity requirement of fluid samples and to facilitate the portability of these systems, the hand held devices and disposable cartridges are designed to be small and lightweight. Research has demonstrated that phlebotomists have difficulty handling these small, lightweight cartridges. The difficulty the phlebotomists have handling the cartridge makes accurate transfers of the samples from the dermal puncture, capillary tube or syringe to the cartridge problematic. As stated above, if the sample does not fill the cartridge properly, the entire cartridge is wasted and must be discarded and a replacement cartridge must be supplied.

In addition, testing of blood includes the risk of transmission of infectious diseases such as human immunodeficiency virus or hepatitis. Therefore, any risk of spilling of blood associated with the use of the sensing device is an obvious concern.

For the foregoing reasons, there is a need for a simple disposable device to collect a volume of blood or other fluid in a capillary tube and introduce these fluids into the disposable cartridge taught by Lauks. The device should be ergonomically designed to facilitate the collection of fluid samples and the introduction of fluid samples into the cartridge. The device also should be separate and distinct from the cartridge thus allowing for sample collection errors to be remedied by discarding only the collection and introduction device rather than the entire cartridge. In addition, the device should reduce or eliminate the risk of spilling fluid samples.

SUMMARY OF THE INVENTION

The present invention is directed to a sample collection device that collects fluid samples and introduces the samples into a sensing device for real time analysis. The collection device provides flexibility and simplicity in the way sample collection is accomplished. The device cooperates with the disposable cartridge of the sensing device to permit quick and easy sample introduction and eliminate the risk of sample spillage. The device is inexpensive to produce, disposable and separate and distinct from the cartridge. If, for some reason, the sample is improperly collected by the collection device, the device can be discarded and a replacement used without having to replace the entire cartridge.

In an exemplary embodiment of the invention, the collection device includes a capillary tube capable of receiving or drawing a fluid sample and introducing the fluid sample into the disposable cartridge, a reservoir chamber capable of receiving a fluid sample and a capillary tube holder capable of supporting one end of the capillary tube in the reservoir chamber to draw the fluid sample by capillary action. The reservoir chamber is an integral part of a closure cap that cooperates with a docking device in the cartridge to secure the collection device in the cartridge.

The collection device collects blood samples in a variety of ways. A phlebotomist may prick a patient's finger with a finger stick to draw a small amount of blood through the dermal puncture. The end of the capillary tube not supported in the reservoir chamber (the introduction end) is placed in the pool of blood formed on the dermal puncture. The blood is drawn into the capillary tube by capillary action. Similarly, the stopper of a Vacutainer™—type vessel filled with blood may be removed and the introduction end of the capillary tube inserted into the vessel. Blood is drawn into the capillary tube from the vessel by capillary action.

Alternatively, a syringe may be utilized with the collection device to collect blood samples from a venous or arterial puncture or from an arterial line. Once the fluid sample has been collected in the syringe, the phlebotomist uses the needle cannula of the syringe to deposit the sample into the reservoir chamber. Alternatively, the phlebotomist may remove the needle cannula from the barrel of the syringe and use the barrel itself to deposit the fluid sample into the reservoir chamber. When sufficient blood collects in the reservoir chamber to contact the end of the capillary tube supported in the reservoir chamber, the blood sample is drawn into the capillary tube by capillary action. Tilting the collection device so the axis of the capillary tube approaches horizontal assists the filling of the capillary tube with fluid sample.

If the sample has not properly filled the collection device, the improperly filled device is discarded and a replacement device used.

After a blood sample has been properly collected in the collection device, the introduction end is inserted through a cartridge docking device into a cavity in the disposable cartridge. The collection device is secured into the docking device by a locking mechanism in the closure cap. A first sealing element, such as an annular seal, in the closure cap forms a first air-tight relation between the closure cap and the cartridge docking device and a second sealing element, such as an annular seal, surrounding the capillary tube forms a second air-tight relation between the capillary tube and the cavity. The first and second air-tight relations, the closure cap, the air bladder and the docking device form a sealed volume. (As used herein, "sealed volume" shall connote any space in which a pressure gradient causes the displacement of a fluid sample contained therein.)

After the sensing device is calibrated and prepared to perform measurements, an air bladder in the cartridge is depressed. Air from the air bladder is forced through an orifice in the docking device into the sealed volume, thereby displacing the fluid sample. The displaced fluid sample exits the introduction end of the capillary tube and passes into the cartridge and across the sensors where measurements are performed.

The exemplary embodiment set forth above collects fluid samples in the capillary tube by contacting its introduction end with a pool of fluid or by filling the reservoir chamber with a syringe. Alternative embodiments used in combination with the variety of blood collection assemblies employed by the medical industry to collect fluid samples are additionally contemplated by this invention. A Vacutainer™—type blood collection system is one such known assembly. Generally, the system consists of a housing, a first needle cannula adapted for insertion into a patient and a second needle cannula at the opposite end of the housing adapted for penetration into an evacuated container for collection of a blood sample. The evacuated container has a resealable penetrable stopper at one end. The evacuated container slides into the housing so that the second needle cannula penetrates the penetrable stopper causing a negative pressure gradient to draw fluid sample from the patient through the housing assembly to collect in the evacuated container.

An alternative embodiment of the invention used in combination with a Vacutainer™—type blood collection system includes an evacuated reservoir chamber having at one end a resealable penetrable stopper and at the other end a puncturable seal, a capillary tube for delivering the fluid sample into the disposable cartridge and a capillary tube holder slidably supporting one end of the capillary tube above the puncturable seal of the reservoir chamber to receive fluid sample. The reservoir chamber is an integral part of a closure cap that cooperates with the docking device in the cartridge to secure the collection device in the cartridge. The evacuated reservoir chamber is filled with a fluid sample by insertion into a Vacutainer™—type blood collection system. The second needle cannula penetrates the penetrable stopper of the evacuated reservoir chamber causing a negative pressure gradient to draw fluid sample from the patient through the housing assembly to collect in the evacuated reservoir chamber. The collection device is removed from the Vacutainer™—type blood collection system without fear of sample spillage as a result of the resealable penetrable stopper. After the evacuated reservoir chamber is properly filled, the collection device is interfaced with the cartridge. During engagement of the collection device with the cartridge, the end of the capillary tube over the puncturable seal is forced downward to puncture the seal to contact the fluid sample. The sample is drawn into the capillary tube.

Hypodermic syringes are also commonly used to collect bodily fluid samples. The syringe generally consists of a hollow barrel fitted with a plunger and needle cannula. Typically, the needle cannula is adapted to the barrel of the syringe by means of a luer fitting. A female luer fitting on the base of the needle cannula mates with a male luer fitting on the forward end of the barrel to secure the needle cannula to the barrel. With the plunger fully depressed, the needle cannula is inserted into a patient's blood vessel. Alternatively, the phlebotomist can tap into an existing arterial line in the patient. As the plunger is withdrawn from the barrel, the negative pressure gradient causes fluid sample to be drawn into the hollow barrel through the needle cannula.

An alternative embodiment of the invention used in combination with a syringe blood collection system includes a female luer fitting capable of receiving a fluid sample from a syringe adapted to a reservoir chamber, a capillary tube for receiving a fluid sample and delivering the sample into the cartridge and a capillary tube holder for holding one end of the capillary tube in the reservoir chamber to draw up the fluid sample by capillary action. The reservoir chamber is an integral part of a closure cap that cooperates with a docking device in the cartridge to secure the collection device in the cartridge.

In operation, after a fluid sample has been collected in the hollow barrel of the syringe, the needle cannula is discarded by releasing the luer fitting connection between the barrel and the needle. The female luer fitting connection adapted to the reservoir chamber is mated to the male luer fitting on the forward end of the barrel to secure the chamber to the barrel. The plunger of the syringe is depressed and fluid sample is injected into reservoir chamber. When sufficient fluid sample collects in the reservoir chamber to contact the end of the capillary tube fluid sample is drawn into the capillary tube by capillary action. Tilting the collection device so the axis of the capillary tube approaches horizontal assists the filling of the capillary tube with fluid sample. The syringe is detached from the collection device after the capillary tube has filled by unscrewing the luer fitting. A male luer fitting cap is mated to female luer fitting of the reservoir chamber to enclose the orifice through which the fluid sample entered the reservoir chamber.

While use of the invention is particularly advantageous in the medical environment and will be described in that context, it will be appreciated that the invention may be practiced in any situation where it is desired to perform analysis of fluid samples.

BRIEF DESCRIPTION OF THE DRAWINGS

These and other features, aspects and advantages of the present invention will become better understood with regard to the following description, appended claims, and accompanying drawings where:

FIG. 7b is a cross-section view of a cap used in conjunction with the collection device illustrated in FIG. 7a;

FIG. 8 is a top view of the collection device illustrated in FIG. 7a;

DETAILED DESCRIPTION OF THE PREFERRED EMBODIMENTS

Collection Device

Figure 1:
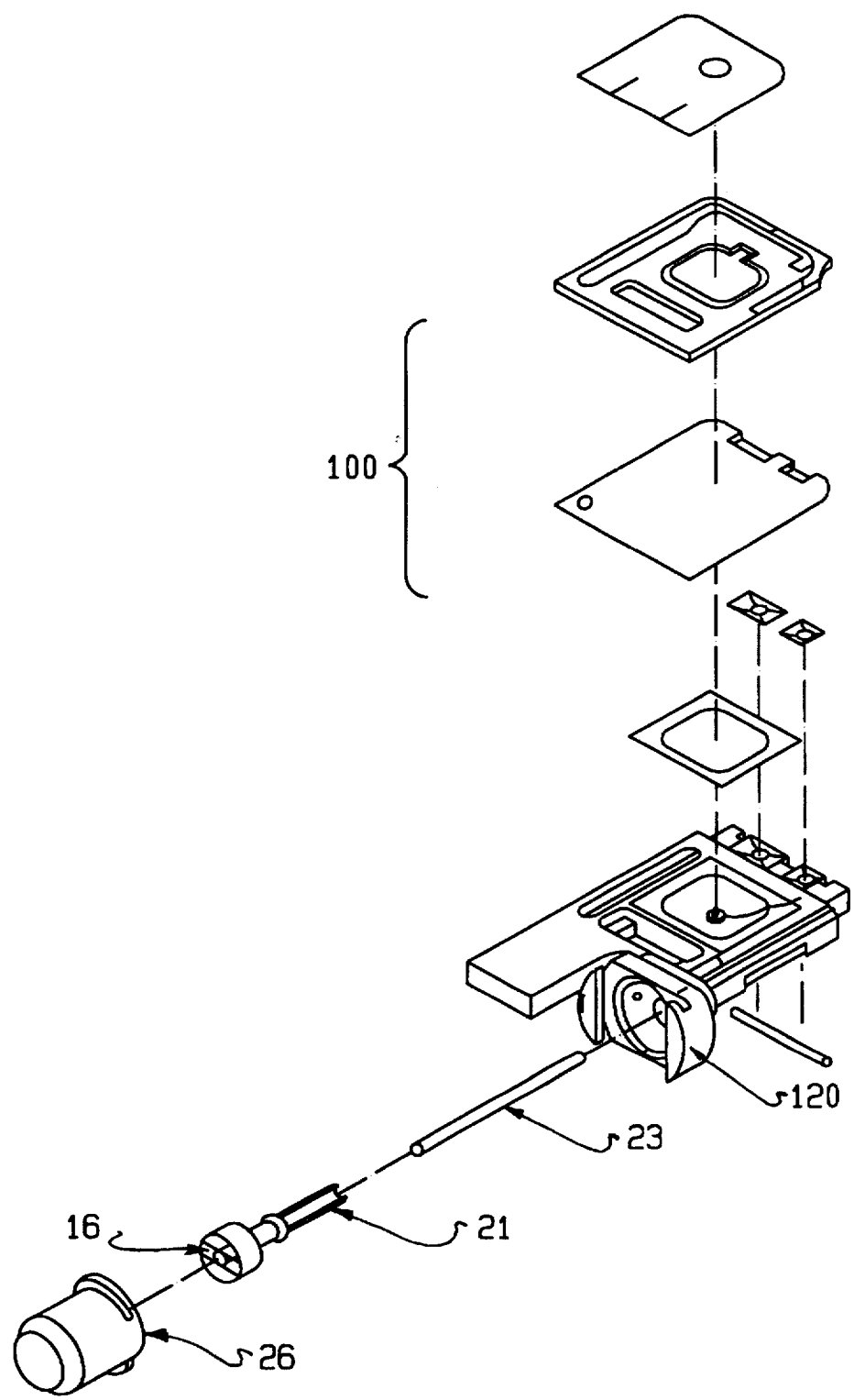
FIG. 1 is a perspective view of a collection device and disposable cartridge embodying features of the present invention for collecting fluid samples and introducing the samples into a sensing device.
Figure 2:
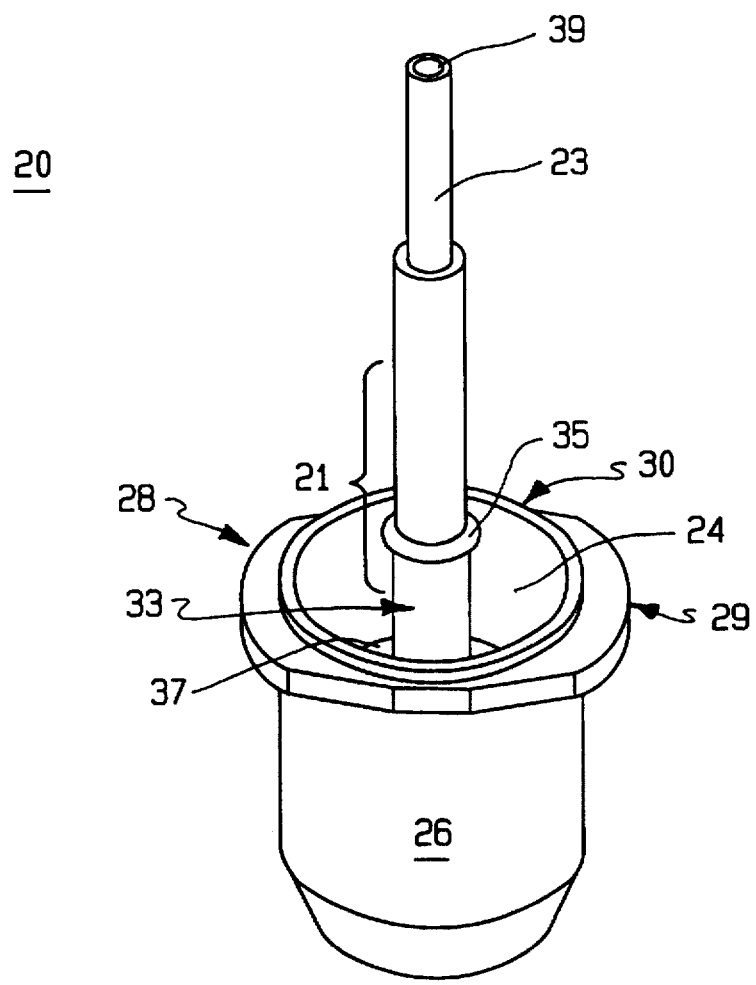
FIG. 2 is a perspective view of the collection device illustrated in FIG. 1.
Figure 3:
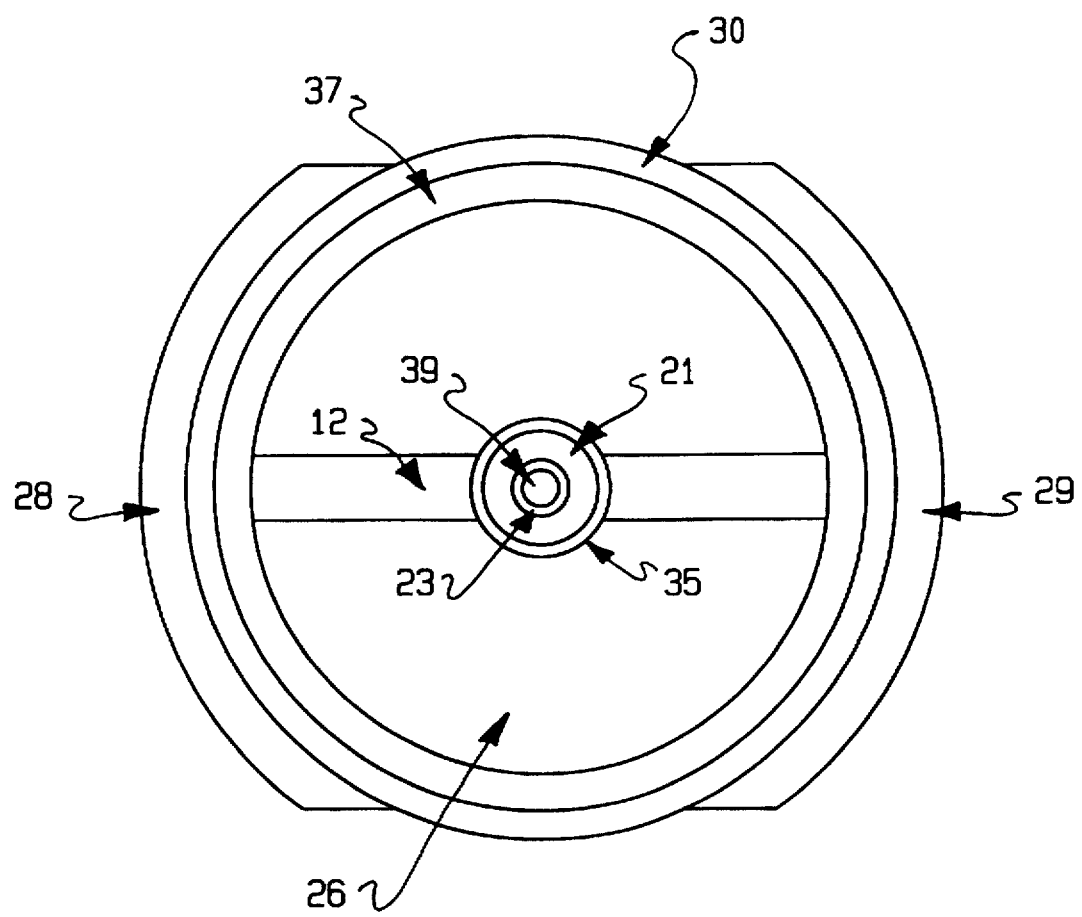
FIG. 3 is a top view of the collection device illustrated in FIG. 1.

Referring to FIGS. 1-3, the collection device 20 of the present invention comprises a capillary tube 23 capable of receiving or drawing a fluid sample and introducing the fluid sample into a disposable cartridge 100, a reservoir chamber 24 capable of receiving a fluid sample, and a capillary tube holder 21 capable of supporting one end of the capillary tube 23 in the reservoir chamber 24 to draw the fluid sample by capillary action into the capillary tube through a sample end 16. The reservoir chamber 24 is an integral part of a closure cap 26 that cooperates with a docking device 120 in the cartridge 100 to secure the collection device 20 in the cartridge 100.

The closure cap 26 comprises a substantially cylindrical body which has an open end and a closed end. The reservoir chamber 24 is formed in the region bounded by the cylindrical body and closed end. Two arcuate flanges 28, 29 are formed at the open end of the cylindrical body. The flanges 28, 29 project out in opposite directions perpendicularly to the axis of the cylindrical body. The flanges 28, 29 cooperate with slots in the docking device 120 in the cartridge 100 to secure the collection device 20 in the cartridge 100. The closure cap 26 may be molded by conventional methods, employing a moldable material such as plastic which is inert to blood components.

A first sealing element 30, for example an annular seal, is deposited along the open end of the closure cap 26. A first air tight relation is made between the first sealing element 30 and the docking device 120 when the collection device 20 is secured in the cartridge 100.

The capillary tube 23 is formed by conventional methods from glass or plastic. The capillary tube 23 contains a through-bore which is precisely dimensioned to contain a sample of predetermined volume. The specifications of the sensing device with respect to the amount of sample required to perform the desired measurement will determine the dimensions of the capillary tube 23 when the collection device 20 is used in combination with a sensing device. Preliminary tests have shown that quantity requirements for the sensing device can be reduced to as little as 35 microliters of fluid sample.

The capillary tube holder 21 is also formed by conventional methods from glass or plastic. The capillary tube holder 21 adds rigidity to the capillary tube 23 thereby reducing the likelihood of breakage. The capillary tube holder 21 comprises a sleeve 33, such as an annular sleeve, a second sealing element 35, such as an annular seal, and a support element 12. The sleeve 33 is supported along the axis of the closure cap 26 by support element 12. Support element 12 projects outwardly from the sleeve perpendicular to the axis of the closure cap 26 and is adapted to the walls of the closure cap 26.

The capillary tube 23 fits snugly within the sleeve 33. The outer surface of the capillary tube 23 forms an air-tight relation with the inner surface of the sleeve 33. The capillary tube 23 is supported along the axis of the closure cap 26 by the capillary tube holder 21. The sample end 16 of the capillary tube 23 is suspended above the closed end of the closure cap 26 by a predetermined distance (the suspension distance). When the reservoir chamber 24 is filled, the level of fluid sample approaches the sample end 16. When the fluid sample contacts the sample end 16, the fluid sample can be drawn into the capillary tube 23 by capillary action. Tilting the collection device 20 so the axis of the capillary tube 23 approaching horizontal assists the filling of the capillary tube 23 with fluid sample. The suspension distance is minimized to reduce the volume of sample needed to be drawn from the patient. However, a minimum suspension distance is maintained to avoid a meniscus from forming between the closed end of the closure cap 26 and the sample end 16 of the capillary tube 23 thereby preventing fluid sample from being drawn into the capillary tube 23.

Figure 11:
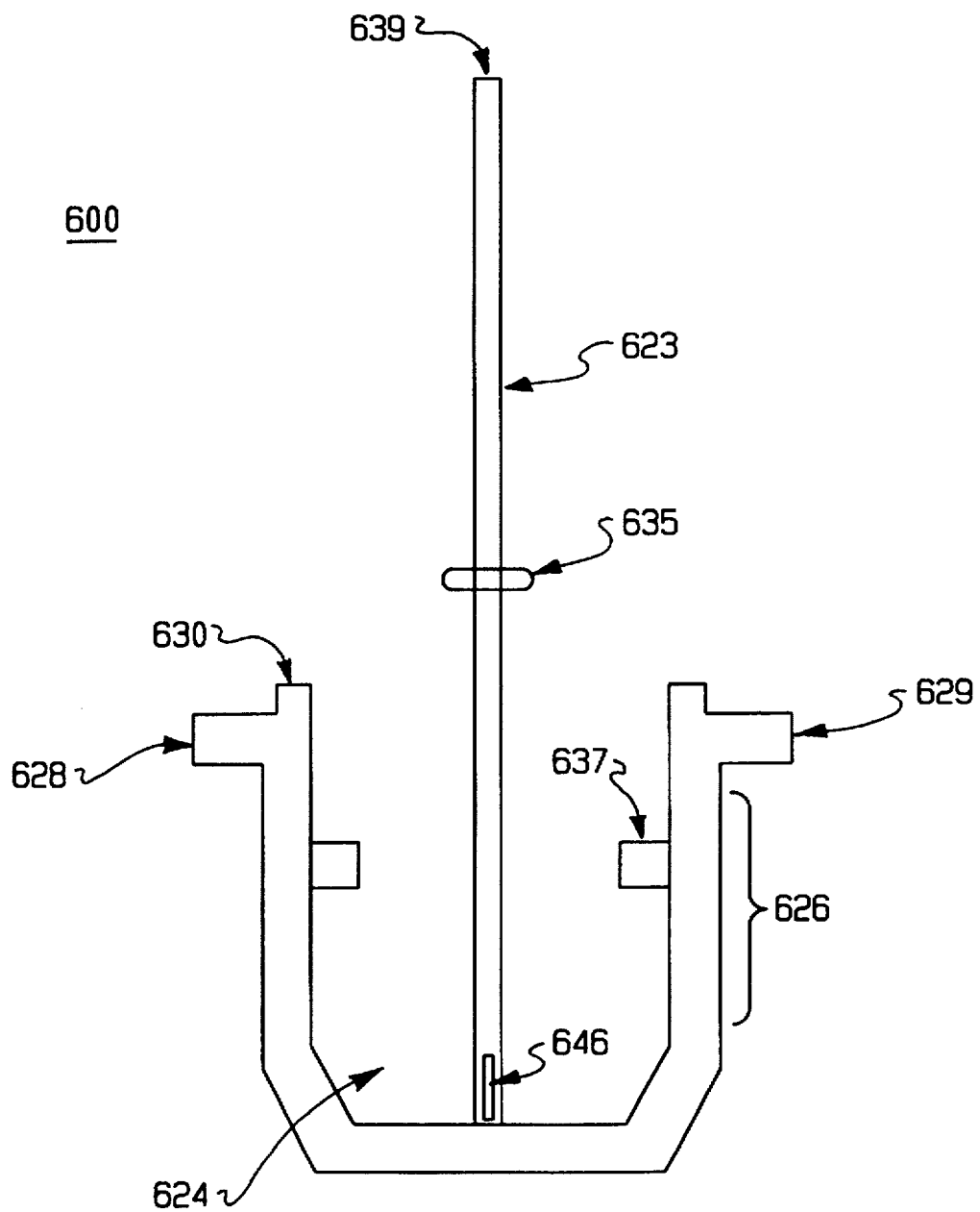
FIG. 11 is a cross-sectional view of another embodiment of a collection device embodying the features of the present invention without a capillary tube holder.

An alternative embodiment of the invention is shown in FIG. 11. This embodiment of the collection device comprises the capillary tube 623 and the reservoir chamber 624 without a capillary tube holder supporting the capillary tube 623. In this embodiment, the base of the capillary tube 623 is affixed to the base of the reservoir chamber 624. One or more openings 646 at the bottom of the capillary tube 623 allows the fluid sample to pass from the reservoir chamber 624 into the capillary tube 623. Accordingly, all references in this specification to fluid sample entering the sample end 16 of a capillary tube shall include without limitation entry of the fluid sample through an opening such as opening 646.

One of the obvious concerns associated with the testing of blood involves the risk of transmission of infectious diseases such as human immunodeficiency virus or hepatitis. To reduce the risk of blood spilling out of the reservoir chamber 24 after a blood sample has been collected in the device, a first barrier is created along the walls of the reservoir chamber 24 to induce the fluid sample to form a meniscus between the walls of the reservoir chamber 24 and the capillary tube 23. The surface tension of the fluid sample prevents unwanted blood from exiting the reservoir chamber 24. To create the barrier, a ledge 37 is formed around the inside circumference of the closure cap 26. The ledge 37 is located between the open end of the closure cap 26 and the sample end 16 of the capillary tube 23. A second barrier is created at the open end of the closure cap 26 between the open end and the capillary tube 23. As with the first barrier, the surface tension of the fluid sample in the meniscus formed between the ledge 37 and the capillary tube 23 prevents unwanted blood from exiting the reservoir chamber 24.

In operation, the collection device 20 collects blood samples in a variety of ways. A phlebotomist may prick a patient's finger with a finger stick to create a dermal puncture through which a small pool of blood forms. The end of the capillary tube 23 not supported in the reservoir chamber 24 (the introduction end 39) is placed in the pool of blood formed on the dermal puncture. The blood is drawn into the capillary tube 23 by capillary action. When a sufficient volume of blood is drawn into the capillary tube 23, the collection device 20 is withdrawn from the dermal puncture and is ready to be analyzed. In a similar fashion, the collection device 20 may collect fluid samples from filled vessels of fluid. For example, the stopper of a Vacutainer™—type vessel filled with blood may be removed and the introduction end 39 of the capillary tube 23 inserted into the vessel. Blood is drawn through the introduction end 39 into the capillary tube 23 from the vessel by capillary action.

Unlike the blood collection methods described above in which blood enters the collection device 20 through the introduction end 39, a syringe or similar device may be used to deposit blood into the collection device 20 through the reservoir chamber 24. After blood has been drawn from a patient in a syringe, the phlebotomist may use the needle cannula of the syringe to direct the blood sample into the reservoir chamber 24. Alternatively, the needle cannula may be removed from the syringe and the blood may be deposited into the reservoir chamber 24 directly from the barrel of the syringe. When sufficient blood collects in the reservoir chamber 24 to contact the end of the capillary tube 23 supported in the reservoir chamber 24, the blood sample is drawn into the capillary tube 23 by capillary action. Tilting the collection device 20 so the axis of the capillary tube 23 approaches horizontal assists the filling of the capillary tube 23 with fluid sample. When a sufficient volume of blood is drawn into the capillary tube 23, the collection device 20 is ready to be analyzed by the sensing device.

Because the collection device 20 is separate and distinct from the more expensive disposable cartridge 100, this allows the process of collecting fluid samples to be separated for the process of introducing the fluid samples into the disposable cartridge 100. This saves both time and expense. If the fluid sample has not properly filled the collection device 20, the improperly filled device is discarded and a replacement used. This eliminates the waste associated with discarding improperly filled disposable cartridges 100.

Introduction into the Disposable Cartridge

Figure 4:
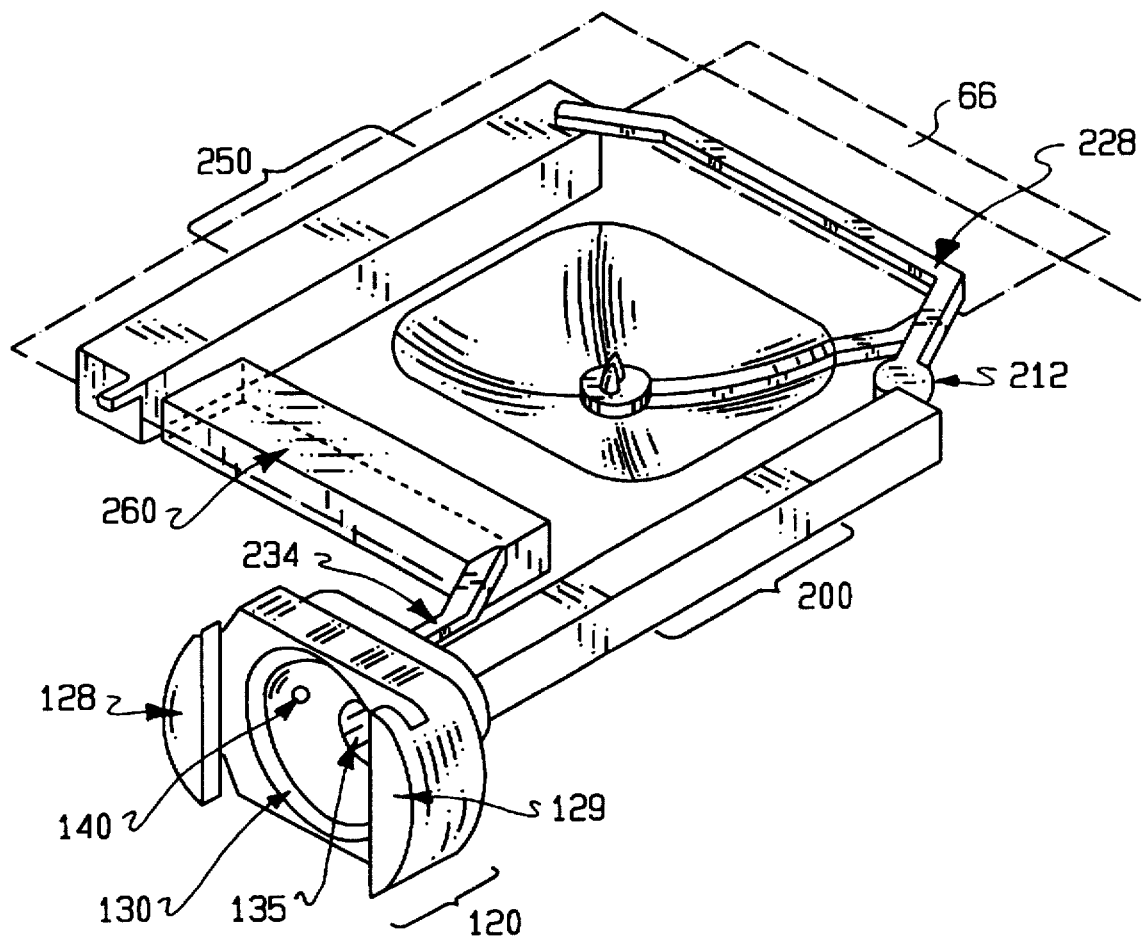
FIG. 4 is a perspective view of the disposable cartridge illustrated in FIG. 1.

After the fluid sample has been properly collected in the collection device 20, the device is ready to be inserted into the disposable cartridge 100 for sample analysis. Referring to FIGS. 1 and 4, the disposable cartridge 100 comprises a first cavity 200 which has a docking device 120 at one end for receiving and mating with the collection device 20 while the other end terminates at an air segment 212. A conduit 228 leads from the air segment 212 past the sensing arrays 66 to a second cavity 250 which serves as a sink. A third cavity 260 serves as an air bladder. When the air bladder 260 is depressed, air is forced down a second conduit 234 to an opening in the docking device 120. The first cavity 200 has a cylindrical opening enclosed therein which cooperates with the second sealing element 35 (FIG. 2) of the collection device 20. After the collection device 20 has been inserted into the cartridge 100, a second air-tight relation is formed between the cylindrical opening and the second sealing element 35.

The docking device 120 of the cartridge includes a circular port 130 capable of receiving the open end of the closure cap 26 to form the first air tight relation, U-shaped slots 128, 129 located outside the circular port 130 which project inwardly in opposite directions perpendicularly to the axis of the circular port 130 and mate with the first and second flanges 28, 29 to secure the collection device 20 in the docking device 120, a first orifice 135 through which the introduction end 39 of the collection device 20 passes to enter the first cavity 200, and a second orifice 140 through which air forced from the depression of the air bladder 260 passes.

In operation, a phlebotomist, holding the closure cap 26, inserts the introduction end 39 of a filled collection device 20 into the first orifice 135 of the docking device 120. As the device is inserted, the alignment of the flanges 28, 29 should be 90 degrees out of phase with the alignment of the U-shaped slots 128, 129. The capillary tube 23 enters and is guided along the first cavity 200 of the cartridge 100. Insertion of the collection device 20 into the cartridge 100 terminates when the open end of the closure cap 26 meets the docking device 120 and enters the circular port 130. The cap is rotated 90 degrees in either direction. As the cap rotates, the flanges 28, 29 engage the U-shaped slots 128, 129 to secured the collection device 20 to the cartridge 100. The first sealing element 30 around the closure cap 26 forms the first air-tight relation between the closure cap 26 and the circular port 130 when the closure cap 26 is secured into the docking device 120. The second sealing element 35 around the capillary tube 23 and capillary tube holder 21 forms the second air-tight relation between the capillary tube 23 and the first cavity 200. The first and second air-tight relations, the reservoir chamber 24 and the docking device 120 create a sealed volume inside the closure cap 26.

After the closure cap 26 is secured to the cartridge 100 and the sealed volume created, the phlebotomist inserts the cartridge 100 with the collection device 20 into the hand-held reader of the sensing device. The hand-held reader performs the necessary operations to calibrate the sensors and prepare them to perform the desired measurements.

Once the sensors are calibrated and prepared to perform measurements, the air bladder 260 in the cartridge 100 is depressed. A predetermined volume of air from the air bladder 260 is forced down the second conduit 234, through the second orifice 140 and into the sealed volume. The forced air creates a positive pressure gradient in the sealed volume. The positive pressure gradient forces the fluid sample to exit the introduction end 39 of the capillary tube 23 past the air segment 212 across the sensors where measurements are performed (air from the air segment 212 forced across the sensors prior to the fluid sample provides a superior wash of the sensors).

Alternative Embodiments

The exemplary embodiment set forth above collects fluid samples in the capillary tube 23 by contacting its introduction end 39 with a pool of fluid or by filling the reservoir chamber 24 with a syringe-like device. Alternative embodiments used in combination with the blood collection assemblies employed by the medical industry to collect blood samples are additionally contemplated by this invention. A Vacutainer™—type blood collection system is one such known assembly. Generally, the system consists of a housing, a first needle cannula adapted for insertion into a patient and a second needle cannula at the opposite end of the housing adapted for penetration into an evacuated container for collection of a blood sample. The evacuated container has a resealable penetrable stopper at one end. The evacuated container slides into the housing so that the second needle cannula penetrates the penetrable stopper causing a negative pressure gradient to draw fluid sample from the-patient through the housing assembly to collect in the evacuated container.

Figure 5:
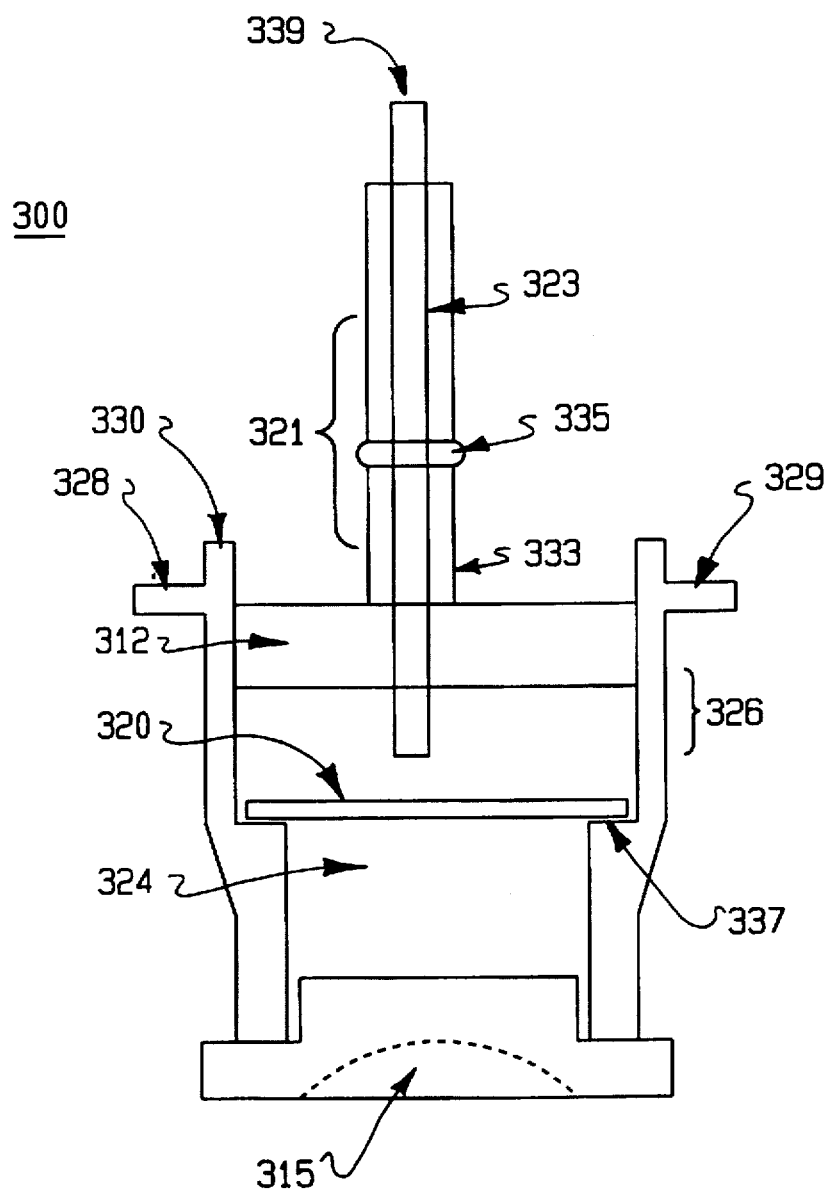
FIG. 5 is a cross-sectional view of another embodiment of a collection device embodying features of the present invention for collecting fluid samples and introducing the samples into a sensing device used in combination with a Vacutainer™—type blood collection system.
Figure 6:
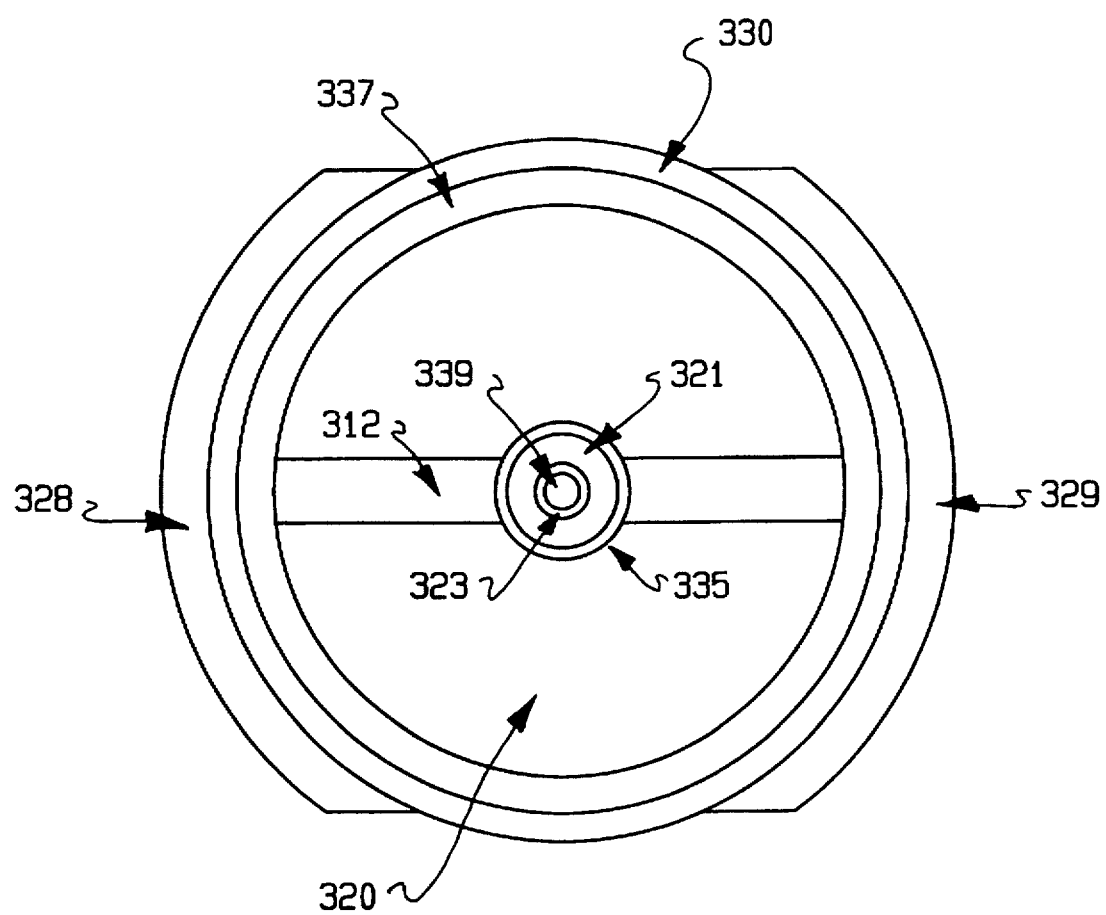
FIG. 6 is a top view of the collection device illustrated in FIG. 5.

An alternative embodiment of the invention used in combination with a Vacutainer™—type blood collection system is illustrated in FIG. 5. This embodiment of the collection device 300 includes an evacuated reservoir chamber 324 having at one end a resealable penetrable stopper 315 and at the other end a puncturable seal 320, a capillary tube 323 for delivering the sample of fluids into the disposable cartridge, and a capillary tube holder 321 slidably supporting the capillary tube 323 above, and guiding it through to puncture, the puncturable seal 320 of the evacuated reservoir chamber 324 to receive the sample of fluids.

The reservoir chamber 324 is an integral part of a closure cap 326 that cooperates with the docking device 120 in the cartridge 100 to secure the collection device 300 in the cartridge 100. The closure cap 326 includes a substantially cylindrical body which has the resealable penetrable stopper 315 at one end and an open end at the other. The puncturable seal 320 is affixed to a ledge 337 around the inside circumference of the closure cap 326. The puncturable seal 320 is preferably produced from a puncturable material capable of maintaining an adequate vacuum over the expected lifetime of the device, such as a polymer laminate aluminum foil. The puncturable seal 320 is affixed to ledge 337 by conventional heat sealing or gluing methods. The puncturable seal 320 provides an air-tight seal that is relatively easy to puncture. The air in the region between the puncturable seal 320, the penetrable stopper 315 and the cylindrical body of the closure cap 326 is evacuated to create the evacuated reservoir chamber 324.

The capillary tube holder 321 comprises a sleeve 333 and a support element 312. The sleeve 333 is supported above the puncturable seal 320 along the axis of the closure cap 326 by support element 312. Support element 312 projects outwardly from the sleeve 333 perpendicular to the axis of the closure cap 326 and is adapted to the walls of the closure cap 326 above the puncturable seal 320. The capillary tube 323 which fits snugly within the sleeve 333 is slidably supported along the axis of the closure cap 326 by the capillary tube holder 321 above the puncturable seal 320.

Similar to the exemplary embodiment of the invention described above and illustrated in FIGS. 1–4, this embodiment of the collection device 300 includes flanges 328, 329 which cooperate with slots 128, 129 in the docking device 120 to secure the collection device 300 to the cartridge 100, first and second sealing elements 330 and 335 which create a first air tight relation between the closure cap 326 and the circular port 130, on the one hand, and a second air tight relation between the capillary tube 323 and the first cavity 200, on the other.

The phlebotomist first inserts the first needle cannula of a Vacutainer™—type blood collection system into a patient's blood vessel. After the Vacutainer™—type blood collection system has been successfully introduced into the patient's blood vessel, the evacuated reservoir chamber 324 is filled with a fluid sample by insertion into the blood collection system. The second needle cannula penetrates the penetrable stopper 315 of the evacuated reservoir chamber 324 causing a negative pressure gradient to draw fluid sample from the patient through the housing assembly to collect in the evacuated reservoir chamber 324. The collection device 300 is removed from the Vacutainer™—type blood collection system without fear of sample spillage as a result of the resealable penetrable stopper 315.

After the evacuated reservoir chamber 324 is properly filled the collection device 300 is introduced into the docking device 120 by inserting the introduction end 339 of the capillary tube 323 into the first orifice 135 of the docking device 120 until the open end of the closure cap 326 enters the circular port 130. The flanges 328, 329 engage the slots 128, 129 of the docking device 120 to secure the collection device 300 to the cartridge 100. The introduction of the fluid collection device 300 with a filled reservoir chamber 324 into the cartridge forces the sample end of the capillary tube 323 downward to puncture the puncturable seal 320 to contact the fluid sample. After pressure equalization, the fluid sample is drawn into the capillary tube 323 by capillary action. Care should be taken to ensure that the puncturable seal 320 does not form an air-tight relation around the capillary tube 323 after being punctured. One alternative solution is implemented by using a capillary tube 323 with an expanded sample end which produces a puncture with a diameter greater than the diameter of the capillary tube 323. A second alternative is implemented by agitating the capillary tube 323 after puncturing the seal 320.

Tilting the collection device 300 so the axis of the capillary tube 323 approaches horizontal assists the filling of the capillary tube 323 with fluid sample.

A sealed volume is created by the first and second air-tight relations, the reservoir chamber 324, the resealable penetrable stopper 315 and the docking device 120. Once the sensors of the sensing device are calibrated and prepared to perform measurements, the air bladder 260 is depressed creating a positive pressure gradient in the sealed volume. The positive pressure gradient forces fluid sample to exit the introduction end 39 of the capillary tube 323 past the capillary break across the sensors where measurements are performed.

Hypodermic syringes are also commonly used to collect bodily fluid samples. The syringe generally consists of a hollow barrel fitted with a plunger and needle cannula. Typically, the needle cannula is adapted to the barrel of the syringe by means of a luer fitting. A female luer fitting on the base of the needle cannula mates with a male luer fitting on the forward end of the barrel to secure the needle cannula to the barrel. With the plunger fully depressed, the needle cannula is inserted into a patient. As the plunger is withdrawn from the barrel, fluid sample is drawn into the hollow barrel through the needle cannula.

Figure 7A:
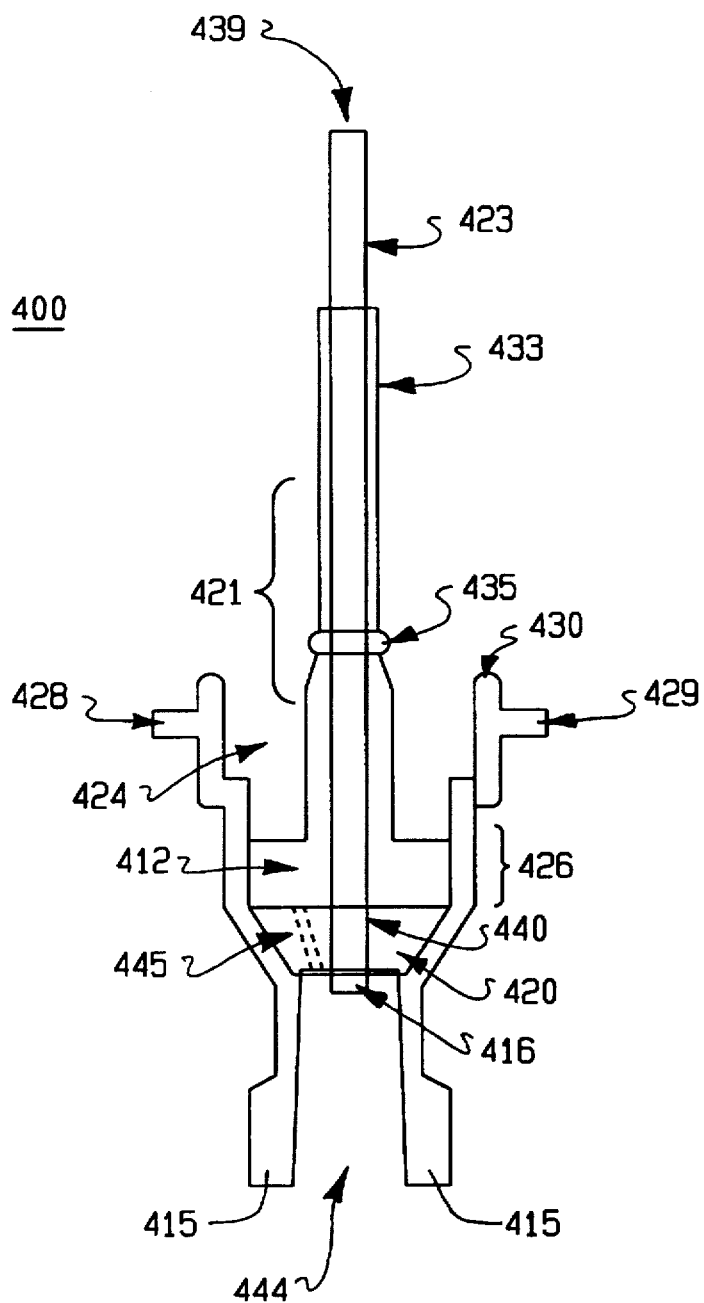
FIG. 7a is a cross-sectional view of another embodiment of a collection device embodying features of the present invention for collecting fluid samples and introducing the samples into a sensing device used in combination with a syringe.
Figure 7B:
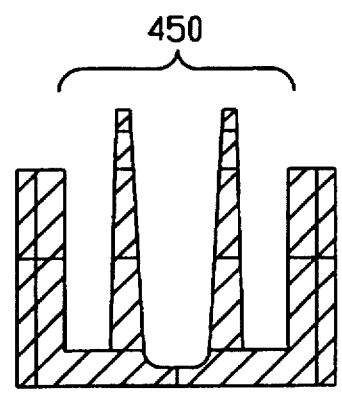
Figure 8:
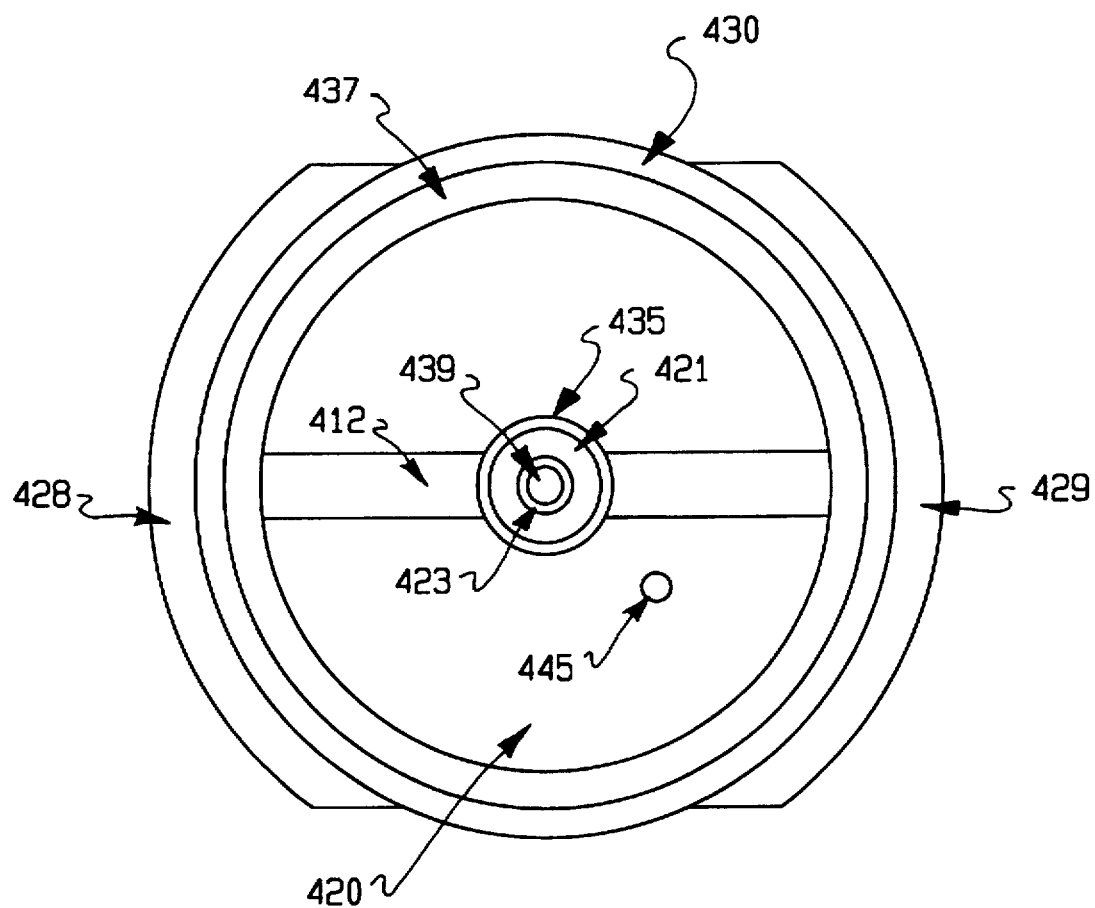

An alternative embodiment of the invention used in combination with a syringe blood collection system is illustrated in FIG. 7a and 7b. This embodiment of the collection device 400 includes a reservoir chamber 424 having adapted to it a female luer fitting 415 capable of receiving a fluid sample from a syringe, a capillary tube 423 for receiving a fluid sample and delivering the sample into the cartridge 100, and a capillary tube holder 421 supporting one end (the sample end 416) of the capillary tube through an opening in the reservoir chamber 424 to draw up the fluid sample by capillary action.

The reservoir chamber 424 is an integral part of a closure cap 426 that cooperates with a docking device 120 in the cartridge to secure the collection device in the cartridge 100. The closure cap 426 includes a substantially cylindrical body which has the female luer fitting 415 at one end and an open end at the other. A barrier 420 is positioned between the luer fitting 415 and the open end of the closure cap 426 to enclose the reservoir chamber 424. A first opening 440 and a second opening 445 pass through barrier 420.

The capillary tube holder 421 is composed of a sleeve 433 and a support element 412. The sleeve 433 is supported above the barrier 420 along the axis of the closure cap 426 by support element 412. Support element 412 projects outwardly from the sleeve perpendicular to the axis of the closure cap 426 and is adapted to the walls of the closure cap 426 above the barrier 420. The capillary tube 423 which fits snugly within the sleeve 433 is supported along the axis of the closure cap 426 by the capillary tube holder 421. The sample end 416 of the capillary tube 423 passes through the first opening 440 in the barrier 420 and enters the reservoir chamber 424.

Similar to the embodiments of the invention described above, this embodiment of the collection device 400 includes flanges 428, 429 which cooperate with slots 128, 129 in the docking device 120 to secure the collection device 400 to the cartridge loo, first and second sealing elements 430 and 435 which create a first air tight relation between the closure cap 426 and the circular port 130, on the one hand, and a second air tight relation between the capillary tube 423 and the first cavity 200, on the other.

In operation, after a fluid sample has been collected in the hollow barrel of the syringe, the needle cannula is discarded after releasing the luer fitting connection between the barrel and the needle. The female luer fitting connection 415 adapted to the reservoir chamber 424 is mated to the male luer fitting on the forward end of the barrel to secure the chamber to the barrel. The plunger of the syringe is depressed and fluid sample is injected through sample end 416 into capillary tube 423 and through second opening 445 into reservoir chamber 424. The syringe is detached from the collection device after the capillary tube has filled by unscrewing the luer fitting 415. A male luer fitting cap 450 is mated to the female luer fitting of the reservoir chamber to enclose and seal the orifice 444 through which the fluid sample entered the reservoir chamber 424. Tilting the collection device 400 so the axis of the capillary tube 423 approaches horizontal assists the filling of the capillary tube 423 with fluid sample.

Similar to the embodiments described above, once the fluid sample has filled the capillary tube 423, the filled collection device 400 is introduced into the docking device 120 by inserting the introduction end 439 of the capillary tube 423 into the first orifice 135 of the docking device 120 until the open end of the closure cap 426 enters the circular port 130. The flanges 428, 429 engage the slots 128, 129 of the docking device 120 to secure the collection device 400 to the cartridge 100. The sealed volume is created by the first and second air-tight relations, the closure cap 426, the male luer fitting cap 450 and the docking device 120. Once the sensors of the sensing device are calibrated and prepared to perform measurements, the air bladder 260 is depressed. Air from the air bladder is forced down the second conduit 234, through the second orifice 140 and into the closure cap 426. Air passes through the second opening 445 in the barrier 420 into the reservoir chamber 424 which creates a positive pressure gradient. The positive pressure gradient forces fluid sample to exit the introduction end 439 of the capillary tube 423 past the capillary break across the sensors where measurements are performed.

Figure 9:
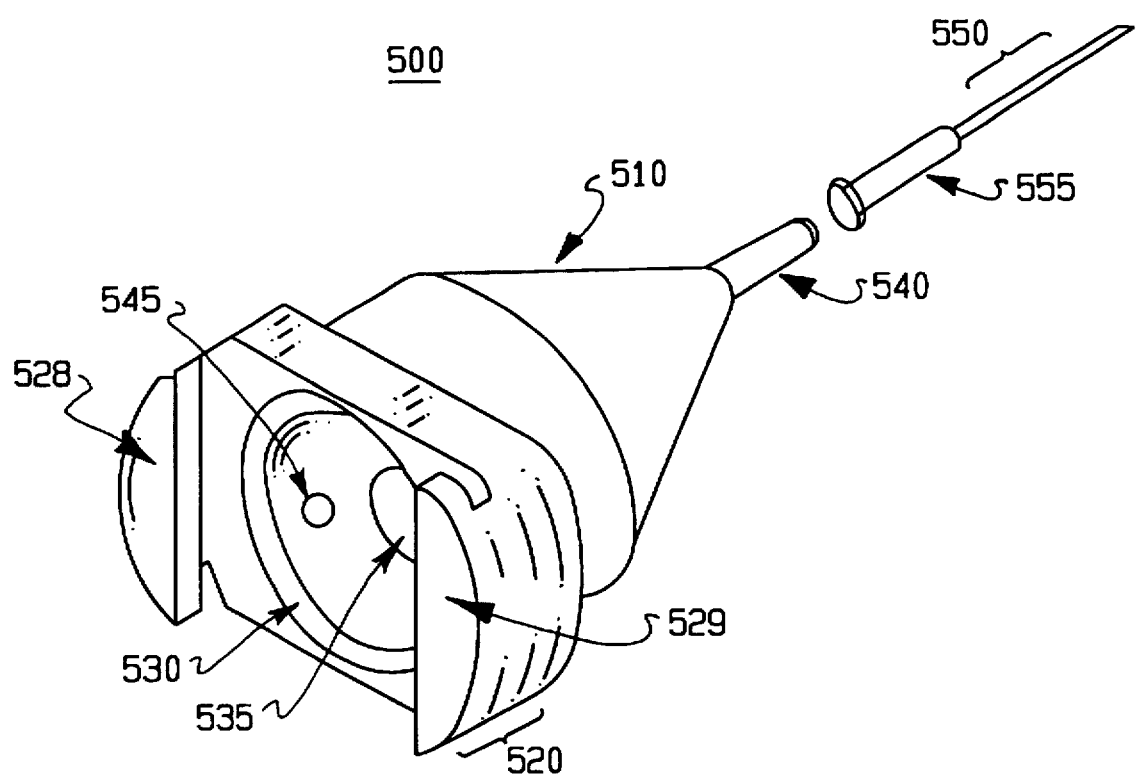
FIG. 9 is a perspective view of the an adapter used in conjunction with the collection device illustrated in FIG. 1.
Figure 10:
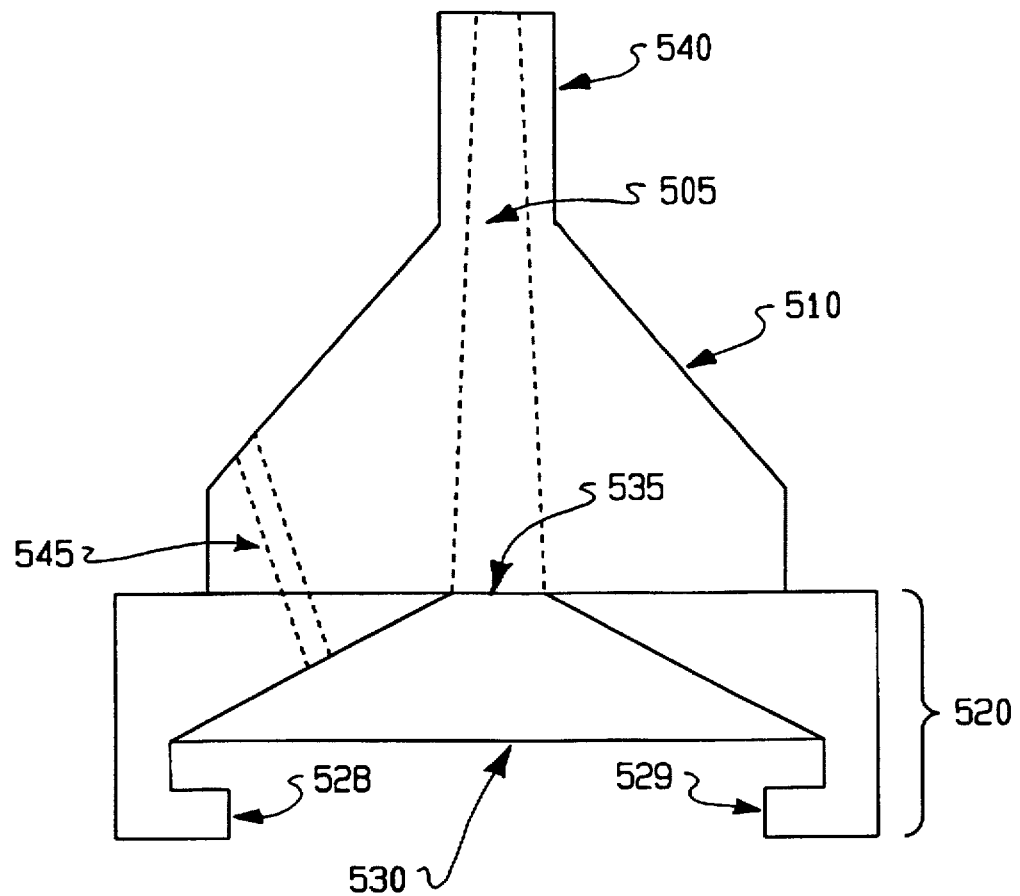
FIG. 10 is a cross-sectional view of the adapter illustrated in FIG. 9.

A further alternative embodiment contemplated by the present invention is illustrated in FIGS. 9 and 10. An adapter 500 is provided to cooperate with the embodiment of the collection device 20 illustrated in FIG. 1–3 to collect a fluid sample in the collection device 20 directly from a patient through a needle cannula 550. The adapter 500 includes a body 510 having a through-bore 505 with an inside diameter slightly greater than the outside diameter of the capillary tube 23/capillary tube holder 21 combination. The adapter also includes a docking device 520 substantially similar to the docking device described above and illustrated in FIG. 4 having a circular port 530 capable of receiving the open end of the closure cap 26, U-shaped slots 528, 529 which mate with the first and second flanges 28, 29 of the collection device 20 to secure the collection device to the adapter 500 and an orifice 535 through which the introduction end 39 of the collection device 20 passes to enter one end of the through-bore 505 of the adapter 500. A male luer fitting 540 is formed about the other end of the through-bore capable of mating with a female luer fitting 555 on the base of a needle cannula 550.

In operation, the introduction end 39 of an empty collection device 20 is inserted through orifice 535 of circular port 530 and is guided along the through-bore 505 of the adapter 500. Insertion of the collection device 20 into the adapter 500 terminates when the open end of the closure cap 26 engages the circular port 530. The cap 26 is rotated 90 degrees in either direction. As the cap 26 rotates, the flanges 28, 29 engage the U-shaped slots 528, 529 to secured the collection device 20 to the adapter 500. The female luer fitting 555 of a needle cannula 550 mates with male luer fitting 540. The introduction end 39 of capillary tube 23 interfaces with the rear end of needle cannula 550.

A phlebotomist inserts the needle cannula 550 of the interlocked collection device 20, adapter 500 and needle cannula 550 into an arterial blood vessel. Immediately after penetration of the needle cannula 550, arterial pressure forces a blood sample through the needle cannula 550 into the introduction end 39 of the capillary tube 23, thereby filling the collection device 20. A vent 545 comprising an air passage through the body of the adapter 500 allows air displaced from the reservoir chamber by the filling fluid sample to exit the reservoir chamber of the collection device 20. Once the collection device 20 is filled the device is removed. The closure cap 26 is again rotated 90 degrees to disengage the flanges 28, 29 from the slots 528, 529. The capillary tube 23 is withdrawn from the through-bore 505 of the adapter 500. The adapter/needle cannula can be discarded and the collection device 20 is ready to be analyzed by the sensing device.

While the invention has been described in conjunction with specific embodiments, it is evident that there are numerous variations in the invention which will be apparent to those skilled in the art in light of the foregoing description.

What is claimed is:

1. A fluid sample collection device comprising:

a reservoir chamber housing circumjacent about a central axis having walls and an open end capable of receiving a fluid sample;

a capillary tube having a first end and a second end; and means for supporting the capillary tube through the open end of the reservoir chamber housing such that an opening substantially encircles the outside of the capillary tube and the first end of the capillary tube is in the reservoir chamber housing.

2. A fluid sample collection device as in claim 1 further comprising a ledge projecting from a wall of the reservoir chamber housing between the opening of the reservoir chamber housing and the first end of the capillary tube.

3. A fluid sample collection device as in claim 1 wherein the reservoir chamber housing is cylindrical and has a bottom.

4. A fluid sample collection device as in claim 3 wherein the first end of the capillary tube is supported above the bottom of the reservoir chamber housing.

5. A fluid sample collection device as in claim 1 wherein the means for supporting the capillary tube includes:

a support element; and a sleeve supported by the support element, the support element projecting outwardly from the central axis and attached to a wall of the reservoir chamber.

6. A fluid sample collection device as in claim 1 wherein the device is adapted for interfacing with a sensing device to introduce a fluid sample into the sensing device for sensing.

7. A fluid sample collection device as in claim 6 wherein the sensing device includes:

a component for receiving the collection device, the component having a cavity adapted for receiving the capillary tube and a port adapted for interfacing with the reservoir chamber housing.

8. A fluid sample collection device as in claim 7 wherein the port includes securing means to secure the collection device to the component.

9. A fluid sample collection device as in claim 7 wherein the reservoir chamber and the port are adapted to permit formation of an air tight relation therebetween.

10. A fluid sample collection device as in claim 7 wherein the capillary tube and the cavity are adapted to permit formation of an air tight relation therebetween.

11. A fluid sample collection device as in claim 7 wherein:

the means for supporting the capillary tube includes a sleeve;

the capillary tube and the sleeve being adapted to permit formation of a first air tight relation therebetween; and the sleeve and the cavity being adapted to permit formation of a second air tight relation therebetween.

12. A fluid sample collection device as in claim 7 wherein the sensing device includes a sample displacement means for displacing a fluid sample in the collection device by forcing the sample through the second end of the capillary tube and into the sensing device.

13. A method of collecting a fluid sample with a fluid sample collection device including a reservoir chamber having an open end capable of receiving a fluid sample, a capillary tube having a first and a second end, and a means for supporting the first end of the capillary tube in the reservoir chamber through the open end such that an opening substantially encircles the outside of the capillary tube, comprising the steps of:

creating a dermal puncture through which a pool of blood forms; and placing the second end of the capillary tube in the pool.

14. A method of collecting a fluid sample with a fluid sample collection device including a reservoir chamber having an open end capable of receiving a fluid sample, a capillary tube having a first and a second end, and a means for supporting the first end of the capillary tube in the reservoir chamber through the open end such that an opening substantially encircles the outside of the capillary tube, wherein the fluid sample collection device is used in combination with a test tube-type vessel for collecting fluid samples, comprising the steps of:

collecting the fluid sample in the vessel; and placing the second end of the capillary tube in the fluid sample collected in the vessel.

15. A method of collecting a fluid sample with a syringe and a fluid sample collection device, the fluid sample collection device including a reservoir chamber having an open end capable of receiving a fluid sample, a capillary tube having a first and a second end, and a means for supporting the first end of the capillary tube in the reservoir chamber through the open end such that an opening substantially encircles the outside of the capillary tube, comprising the steps of:

collecting the fluid sample in the syringe; and depositing fluid sample from the syringe into the reservoir chamber with the syringe through the opening.

* * * * *